(12) United States Patent
Tybinkowski et al.

(10) Patent No.: US 9,363,876 B2
(45) Date of Patent: Jun. 7, 2016

(54) COMPUTERIZED TOMOGRAPHY (CT) IMAGING SYSTEM WITH IMPROVED X-RAY TUBE MOUNT

(71) Applicant: NeuroLogica Corp., Danvers, MA (US)

(72) Inventors: Andrew P. Tybinkowski, Boxford, MA (US); Daehyung Park, Yongin-Si (KR); Pilyong Oh, Gwangmyeong-Si (KR); Eric Bailey, North Hampton, NH (US)

(*) Notice: Subject to any disclaimer, the term of this patent is extended or adjusted under 35 U.S.C. 154(b) by 99 days.

(21) Appl. No.: 14/249,106

(22) Filed: Apr. 9, 2014

(65) Prior Publication Data

US 2014/0301526 A1    Oct. 9, 2014

Related U.S. Application Data

(60) Provisional application No. 61/809,917, filed on Apr. 9, 2013.

(51) Int. Cl.
  *H05G 1/04* (2006.01)
  *G01N 23/04* (2006.01)
  *A61B 6/03* (2006.01)
  *A61B 6/00* (2006.01)

(52) U.S. Cl.
  CPC *H05G 1/04* (2013.01); *A61B 6/035* (2013.01); *A61B 6/40* (2013.01); *A61B 6/4429* (2013.01); *G01N 23/046* (2013.01); *G01N 2223/308* (2013.01)

(58) Field of Classification Search
  CPC ........ A61B 6/035; A61B 6/4429; H05G 1/02; H05G 1/04
  USPC .......................... 378/4, 15, 193, 197
  See application file for complete search history.

(56) References Cited

U.S. PATENT DOCUMENTS

| 4,115,695 | A | 9/1978 | Kelman |
| 4,366,577 | A | 12/1982 | Brandt |
| 4,658,408 | A | 4/1987 | Amor et al. |
| 6,519,312 | B1* | 2/2003 | Tybinkowski ........... H05G 1/02 378/15 |
| 2003/0035506 | A1 | 2/2003 | Tybinkowski et al. |
| 2011/0058643 | A1* | 3/2011 | Lamaitre ................ A61B 6/032 378/4 |

* cited by examiner

*Primary Examiner* — Jurie Yun
(74) *Attorney, Agent, or Firm* — Pandiscio & Pandiscio

(57) ABSTRACT

An X-ray tube mount for mounting an X-ray tube assembly to the rotating disk assembly of a CT imaging system, said X-ray tube mount including a housing having an inner end and an outer end, wherein said inner end of said housing is located closer to the center of rotation of the rotating disk assembly than said outer end of said housing; and at least one mounting construct for mounting said housing to the rotating disk assembly, wherein said at least one mounting construct is disposed intermediate said inner end of said housing and said outer end of said housing.

15 Claims, 15 Drawing Sheets

NATURAL FREQUENCY OF X-RAY TUBE MOUNT TO SEE STIFFNESS (IMPROVED MOUNTING)

Mode 2, bending (840.6Hz)

NATURAL FREQUENCY OF X-RAY TUBE MOUNT TO SEE STIFFNESS (IMPROVED MOUNTING)

Mode 1, bending (581.6Hz)

COMPUTERIZED TOMOGRAPHY (CT) IMAGING SYSTEM WITH IMPROVED X-RAY TUBE MOUNT

REFERENCE TO PENDING PRIOR PATENT APPLICATION

This patent application claims benefit of prior U.S. Provisional Patent Application Ser. No. 61/809,917, filed Apr. 9, 2013 by Andrew P. Tybinkowski et al. for COMPUTERIZED TOMOGRAPHY (CT) IMAGING SYSTEM WITH IMPROVED X-RAY TUBE MOUNT, which patent application is hereby incorporated herein by reference.

FIELD OF THE INVENTION

This invention relates to imaging systems in general, and more particularly to computerized tomography (CT) imaging systems.

BACKGROUND OF THE INVENTION

In many situations, it can be desirable to image the interior of opaque objects. By way of example but not limitation, in the medical field, it can be desirable to image the interior of a patient's body so as to allow internal body structures to be viewed without physically penetrating the skin of the patient. By way of further example but not limitation, in the security field, it can be desirable to image the interior of a container and/or carrying case so as to allow the contents of the container and/or carrying case to be viewed without physically opening the container and/or carrying case.

The present invention will hereinafter be discussed in the context of medical imaging, however, it should be appreciated that the present invention is also applicable to other types of imaging, e.g., security screening, equipment analysis, etc.

Computerized Tomography (CT) has emerged as a key imaging modality in the medical field. CT imaging systems generally operate by directing X-rays into the body from a variety of positions, detecting the X-rays passing through the body, and then processing the detected X-rays so as to build a computer model of the patient's anatomy. This computer model can then be visualized so as to provide images of the patient's anatomy.

By way of example but not limitation, and looking now at FIGS. 1 and 2, there is shown a CT imaging system 5. CT imaging system 5 generally comprises a torus 10 which is supported by a base 15. Torus 10 and base 15 together comprise a frame for CT imaging system 5. A center opening 20 (which is sometimes referred to as an axial opening) is formed in torus 10. Center opening 20 receives the patient anatomy which is to be scanned.

Looking next at FIG. 3, torus 10 generally comprises an X-ray tube assembly 25, an X-ray detector assembly 30, and a rotating disk assembly 35. X-ray tube assembly 25 and X-ray detector assembly 30 are mounted to rotating disk assembly 35 in diametrically-opposing relation, such that the X-ray beam 40 (generated by X-ray tube assembly 25 and detected by X-ray detector assembly 30) is passed through the patient anatomy disposed in center opening 20. Inasmuch as X-ray tube assembly 25 and X-ray detector assembly 30 are mounted on rotating disk assembly 35 so that they are rotated as a unit concentrically about center opening 20, X-ray beam 40 will be passed through the patient's anatomy and detected along a full range of radial positions, so as to enable CT imaging system 5 to create a "slice" image of the anatomy penetrated by the X-ray beam. Furthermore, by moving the patient relative to CT imaging system 5 during scanning (or, alternatively, by moving CT imaging system 5 relative to the patient during scanning), a series of slice images can be acquired, and thereafter appropriately processed, so as to create a three-dimensional (3D) computer model of the scanned anatomy.

As noted above, X-ray tube assembly 25 and X-ray detector assembly 30 are mounted on rotating disk assembly 35 so that they are rotated as a unit concentrically about center opening 20.

In general, and looking now at FIGS. 4-9, X-ray tube assembly 25 is mounted to rotating disk assembly 35 using an X-ray tube mount 45. More particularly, X-ray tube mount 45 comprises a housing which is typically formed in two sections, an outer section 50 and an inner section 55, with X-ray tube assembly 25 being captured between outer section 50 and inner section 55. As used herein, the terms "outer" and "inner" are characterized in the context of the center of rotation of rotating disk assembly 35, i.e., inner section 55 is disposed closer to the center of rotation of rotating disk assembly 35 than outer section 50.

Outer section 50 of X-ray tube mount 45 is secured to rotating disk assembly 35, whereby to secure X-ray tube mount 45 (and hence X-ray tube assembly 25) to rotating disk assembly 35. More particularly, outer section 50 of X-ray tube mount 45 comprises two feet 60 which are secured to rotating disk assembly 35 via bolts 63 which extend through holes 65 in feet 60 and engage drum mounts 66 (e.g., brackets). Thus, holes 65 in feet 60 provide mounting constructs for mounting X-ray tube mount 45 to rotating disk assembly 35. Note that holes 65 and bolts 63 are disposed at the outer end of X-ray tube mount 45, i.e., near the outer circumference of rotating disk assembly 35. Note also that the outermost portion of outer section 50 of X-ray tube mount 45 comprises first and second lateralmost edges 67A, 67B, and that holes 65 (i.e., the mounting constructs) are disposed laterally inboard of first and second lateralmost edges 67A, 67B.

Inner section 55 of X-ray tube mount 45 includes a window 70 which emits the X-rays from X-ray tube assembly 25.

In addition to the foregoing, it should also be appreciated that X-ray tube assembly 25 generally comprises a so-called "moving anode" X-ray tube. In a moving anode X-ray tube, which is commonly used in medical scanners due to the higher energy requirements associated with medical imaging, the anode 71 (FIG. 6) of the X-ray tube assembly 25 is mounted on a shaft 72 which is rotated at a high rate of speed (e.g., up to 10,000 revolutions per minute) within the X-ray tube assembly. The cathode 73 emits electrons which are drawn to anode 71, with X-rays 40 being emitted off the anode and passing out window 70. It should be appreciated that in a moving anode X-ray tube, cathode 73 is radially displaced from the axis of rotation 74 of anode 71 (which axis of rotation 74 is sometimes referred to as "the longitudinal axis of the X-ray tube"). It should also be appreciated that in a moving anode X-ray tube, delicate bearings must be provided for shaft 72, etc., in order to sustain the high rate of rotation required for the moving anode.

It will be appreciated that any instability in the mounting of X-ray tube assembly 25 to rotating disk assembly 35 can produce variations in the X-ray beam characteristics, and hence can negatively affect the quality of the images generated by CT imaging system 5. In addition, since X-ray tube assembly 25 typically contains rapidly moving parts (e.g., an anode rotating at up to 10,000 revolutions per minute), any instability in the mounting of X-ray tube assembly 25 to rotating disk assembly 35 can cause excessive wear of the parts (e.g., bearings) within X-ray tube assembly 25, which can shorten the life of the X-ray tube assembly. It will be appreciated that, inasmuch as the X-ray tube assembly is a relatively expensive component of a CT imaging system, excessive wear of the parts (e.g., bearings) within X-ray tube assembly 25 is undesirable.

Historically, the aforementioned X-ray tube mount 45 (comprising outer section 50 and inner section 55, with outer section 50 comprising feet 60 which are secured to rotating disk assembly 35 via bolts 63 which extend through holes 65 in feet 60 and engage drum mounts 66) has performed acceptably. However, interest has now arisen in rotating the rotating disk assembly 35 with significantly increased speeds, e.g., at 270 revolutions per minute. At these increased speeds, the forces imposed on X-ray tube assembly 25 and X-ray tube mount 45 are quite large, and the conventional X-ray tube mount 45 has proven incapable of providing the requisite stability for X-ray tube assembly 25 as rotating disk assembly 35 is rotated. Among other things, instability in the mounting of X-ray tube assembly 25 to rotating disk assembly 35 has negatively affected the quality of the images generated by CT imaging system 5 and has caused excessive wear of the parts (e.g., bearings) within X-ray tube assembly 25, which shortens the life of the X-ray tube assembly.

Therefore, a new and improved X-ray tube mount is needed for mounting the X-ray tube assembly to the rotating disk assembly in a CT imaging system.

SUMMARY OF THE INVENTION

The present invention provides a new and improved X-ray tube mount for mounting the X-ray tube assembly to the rotating disk assembly in a CT imaging system. Among other things, this new and improved X-ray tube mount provides significantly increased stability for an X-ray tube assembly, such that the rotating disk assembly can be rotated with significantly increased speeds, e.g., 270 revolutions per minute, while still providing the requisite stability for the X-ray tube assembly.

In one preferred form of the present invention, there is provided an X-ray tube mount for mounting an X-ray tube assembly to the rotating disk assembly of a CT imaging system, said X-ray tube mount comprising:

a housing having an inner end and an outer end, wherein said inner end of said housing is located closer to the center of rotation of the rotating disk assembly than said outer end of said housing; and at least one mounting construct for mounting said housing to the rotating disk assembly, wherein said at least one mounting construct is disposed intermediate said inner end of said housing and said outer end of said housing.

In another preferred form of the present invention, there is provided apparatus comprising:

an X-ray tube mount for mounting an X-ray tube assembly to the rotating disk assembly of a CT imaging system, said X-ray tube mount comprising:

a housing having an inner end and an outer end, wherein said inner end of said housing is located closer to the center of rotation of the rotating disk assembly than said outer end of said housing; and at least one mounting construct for mounting said housing to the rotating disk assembly, wherein said at least one mounting construct is disposed intermediate said inner end of said housing and said outer end of said housing; and an X-ray tube assembly disposed within said housing.

In another preferred form of the present invention, there is provided a method for scanning an object, said method comprising:

providing a computer tomography (CT) imaging system comprising a rotating disk assembly having an axial opening formed therein, an X-ray tube assembly mounted to said rotating disk assembly on one side of said axial opening, and an X-ray detector assembly mounted to said rotating disk assembly on the opposing side of said axial opening, wherein said X-ray tube assembly is mounted to said rotating disk assembly using an X-ray tube mount, wherein said X-ray tube mount comprises:

a housing having an inner end and an outer end, wherein said inner end of said housing is located closer to the center of rotation of said rotating disk assembly than said outer end of said housing; and at least one mounting construct for mounting said housing to said rotating disk assembly, wherein said at least one mounting construct is disposed intermediate said inner end of said housing and said outer end of said housing;

positioning the object to be scanned within said axial opening of said rotating disk assembly; and while rotating said rotating disk assembly, passing X-rays from said X-ray tube assembly through the object and detecting X-rays passing through the object with said X-ray detector.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

DETAILED DESCRIPTION OF THE PREFERRED EMBODIMENTS

Figure 1:
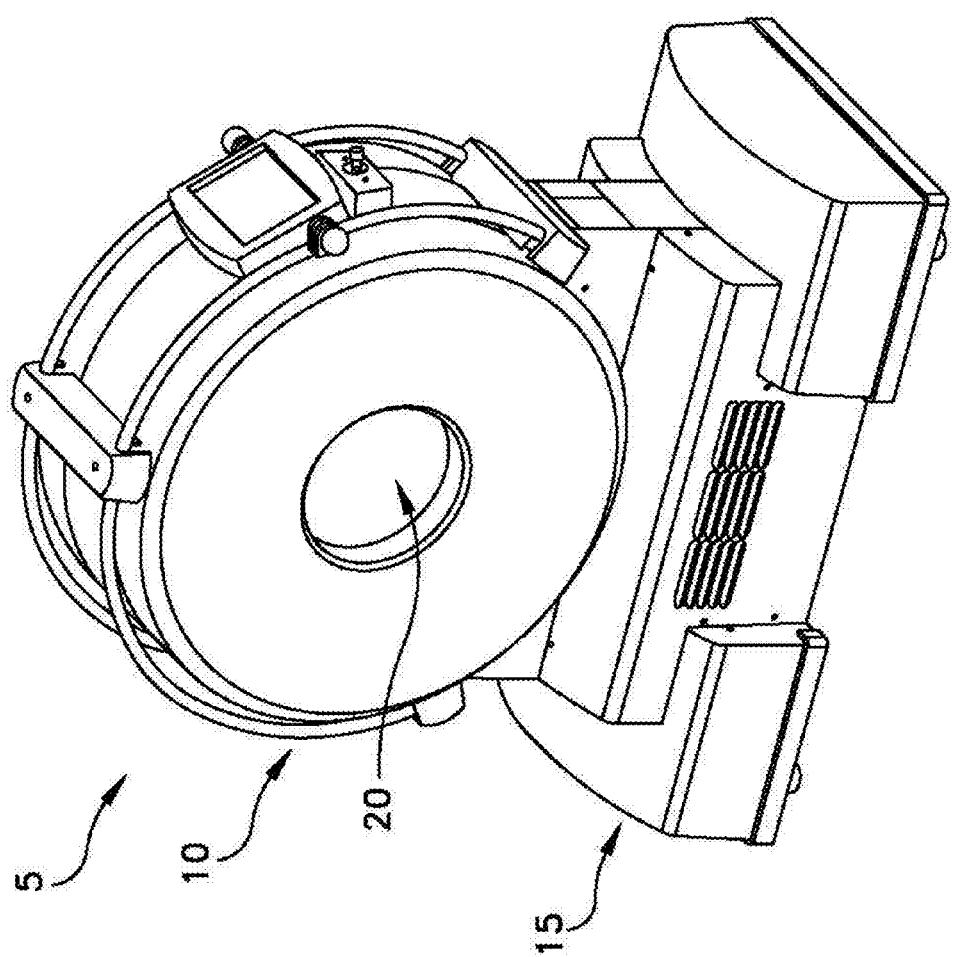
FIGS. 1-3 are schematic views showing the general construction of a CT imaging system.
Figure 2:
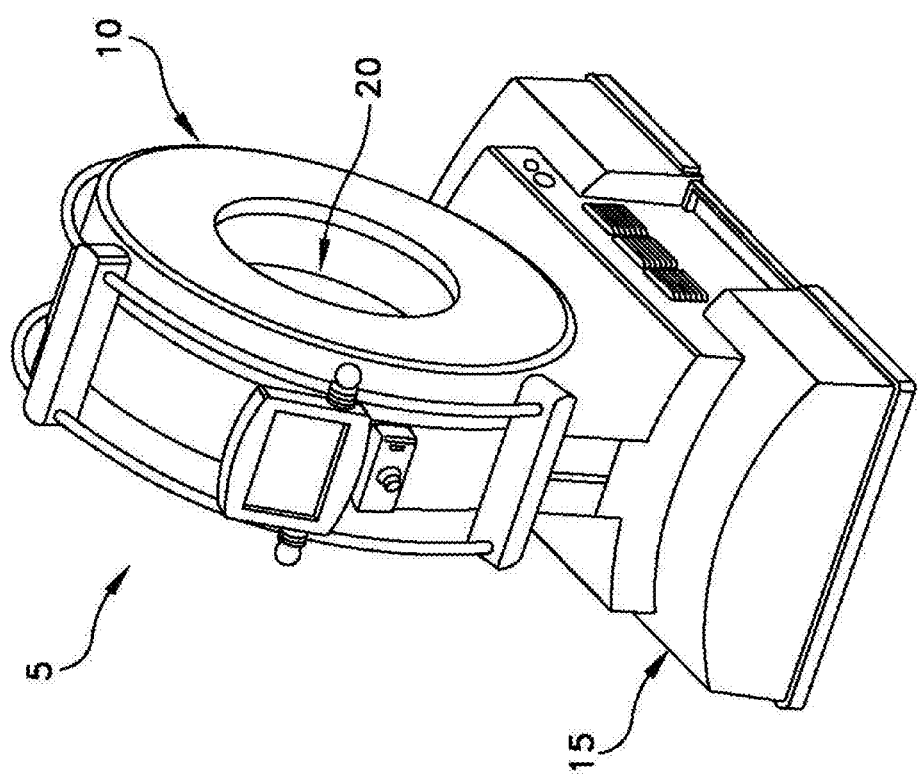
Figure 3:
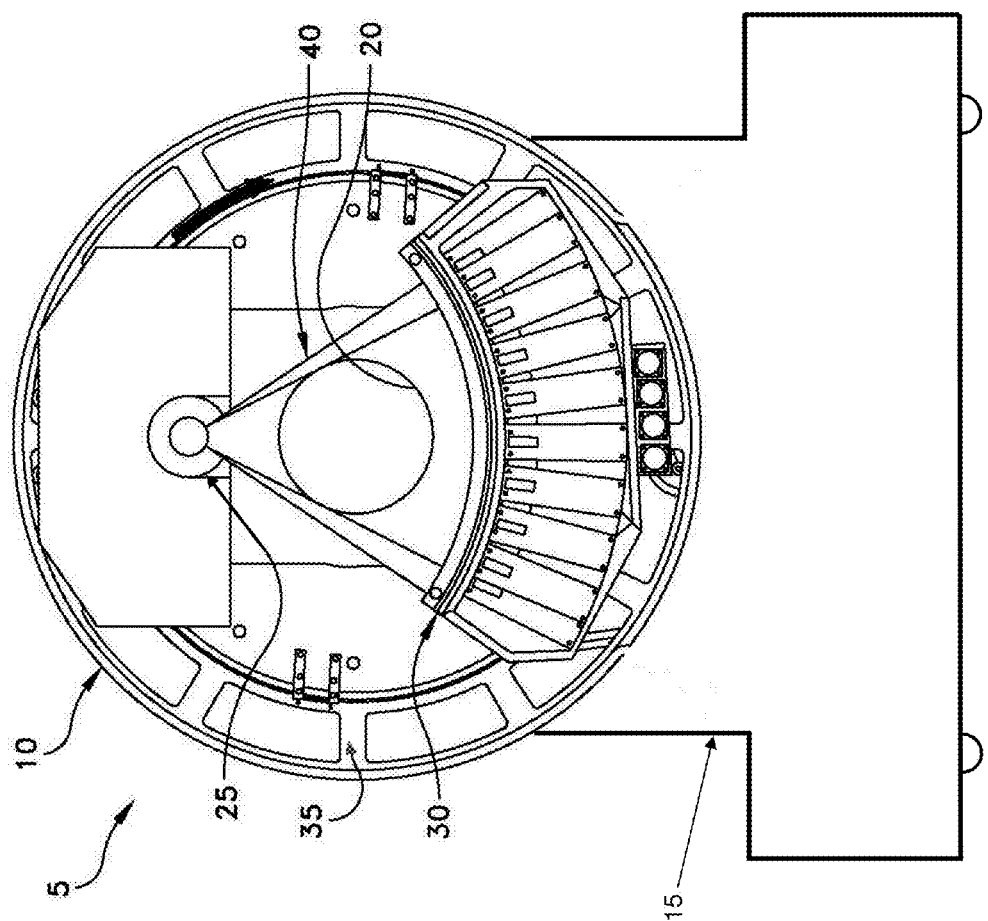

The present invention provides a new and improved X-ray tube mount for mounting the X-ray tube assembly to the rotating disk assembly in a CT imaging system. Among other things, this new and improved X-ray tube mount provides significantly increased stability for an X-ray tube assembly, such that the rotating disk assembly can be rotated with significantly increased speeds, e.g., 270 revolutions per minute, while still providing the requisite stability for the X-ray tube assembly.

More particularly, and looking now at FIGS. 10-15, there is shown a new and improved X-ray tube mount 145 for mounting X-ray tube assembly 25 to rotating disk assembly 35. The new and improved X-ray tube mount 145 comprises a housing which is formed in two sections, an outer section 150 and an inner section 155, with X-ray tube assembly 25 being captured to X-ray tube mount 145 between outer section 150 and inner section 155. Again, as used herein, the terms "outer" and "inner" are characterized in the context of the center of rotation of rotating disk assembly 35, i.e., inner section 155 lies closer to the center of rotation of rotating disk assembly 35 than outer section 150.

Inner section 155 is secured to rotating disk assembly 35, whereby to secure X-ray tube mount 145 (and hence X-ray tube assembly 25) to rotating disk assembly 35. More particularly, with the present invention, inner section 155 of X-ray tube mount 145 comprises a pair of flanges 160 which extend parallel to the longitudinal axis of X-ray tube assembly 25 (i.e., parallel to the axis of rotation 74 of anode 71) and are secured to rotating disk assembly 35 via bolts 163 which extend through holes 165 in flanges 160 and engage drum mounts 166 (e.g., brackets). Thus, holes 165 in flanges 160 provide mounting constructs for mounting X-ray tube mount 145 to rotating disk assembly 35. Note that the outermost portion of outer section 150 of X-ray tube mount 145 comprises first and second lateralmost edges 167A, 167B, and that holes 165 in flanges 160 of inner section 155 (i.e., the mounting constructs) are disposed laterally outboard of first and second lateralmost edges 167A, 167B.

Figure 4:
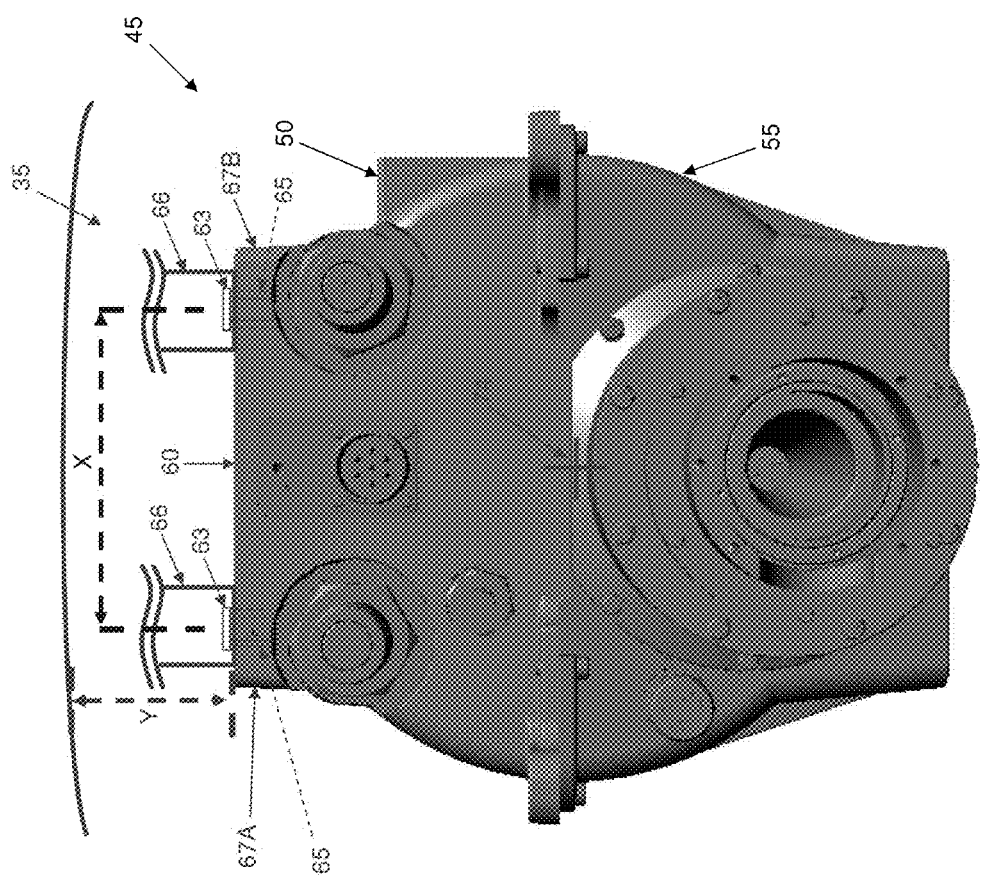
FIGS. 4-9 are schematic views showing a conventional X-ray tube mount for mounting an X-ray tube assembly to the rotating disk assembly of a CT imaging system.
Figure 5:
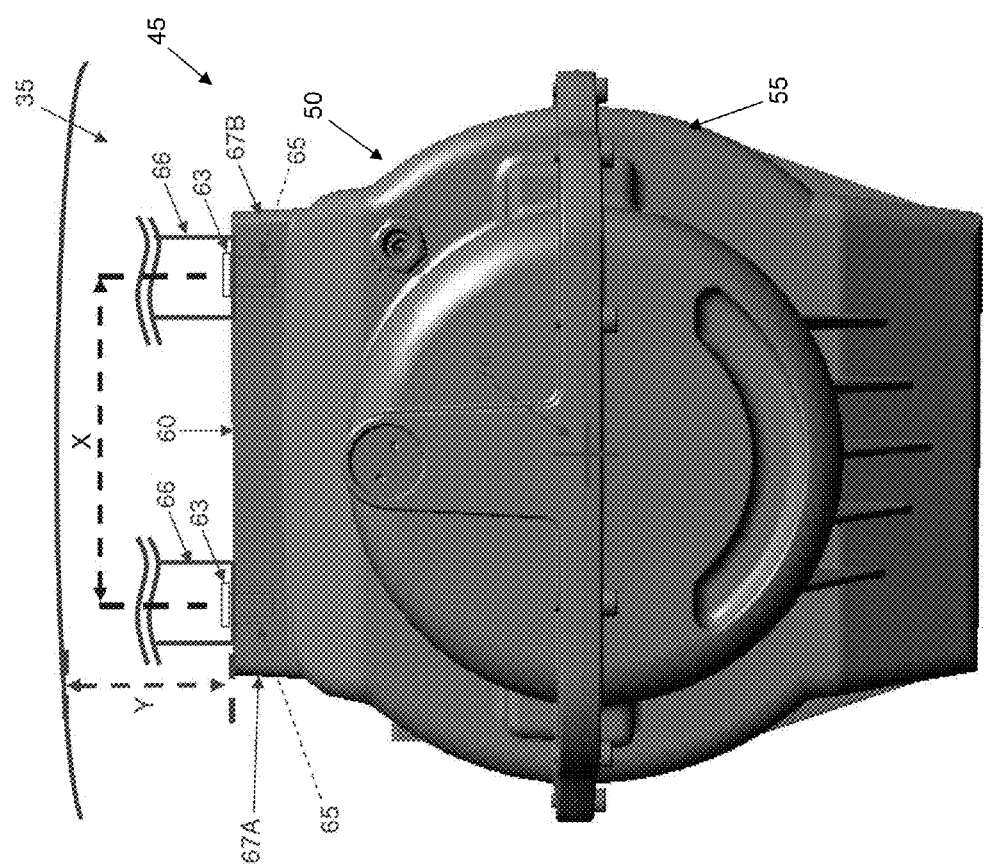
Figure 6:
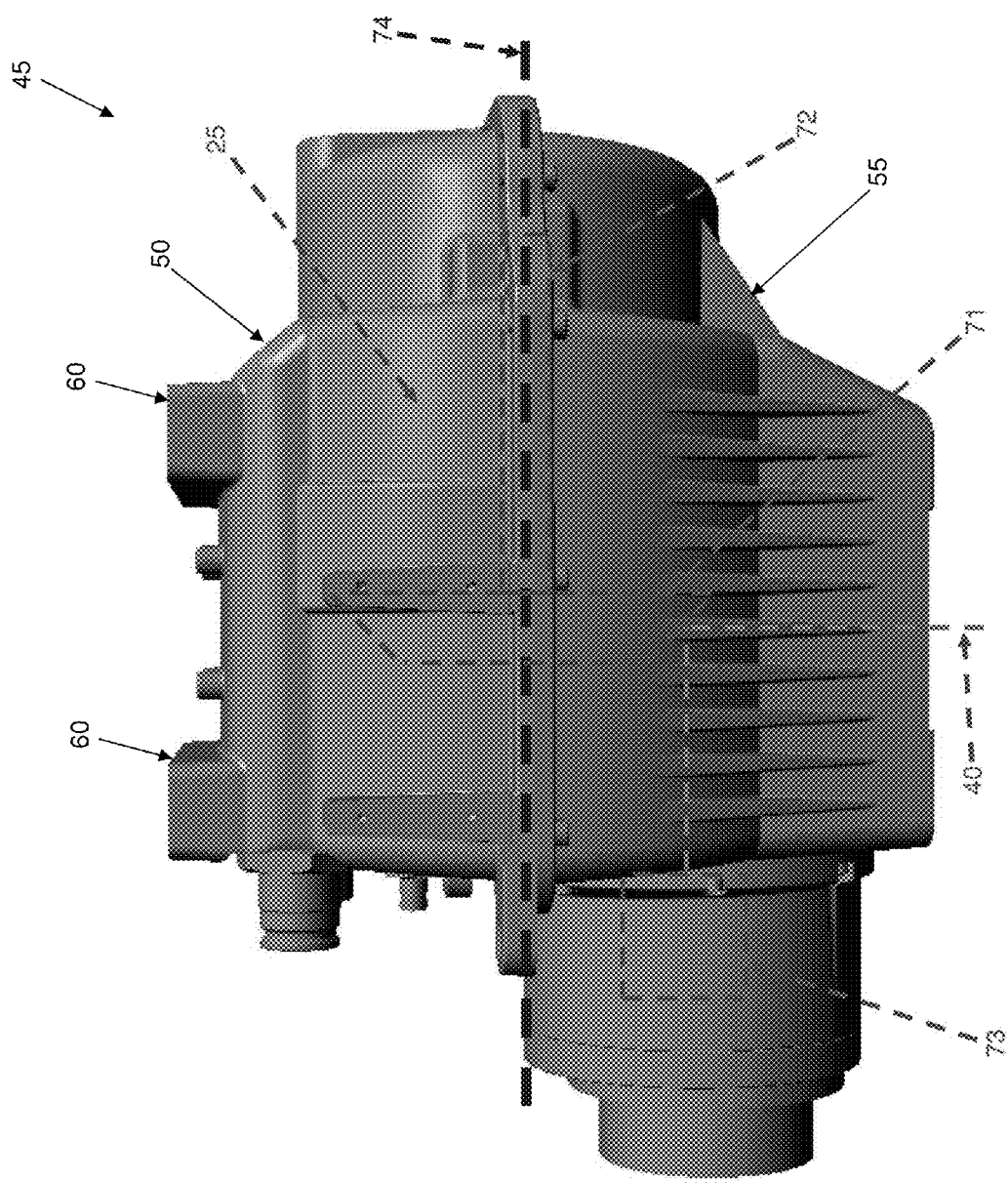
Figure 8:
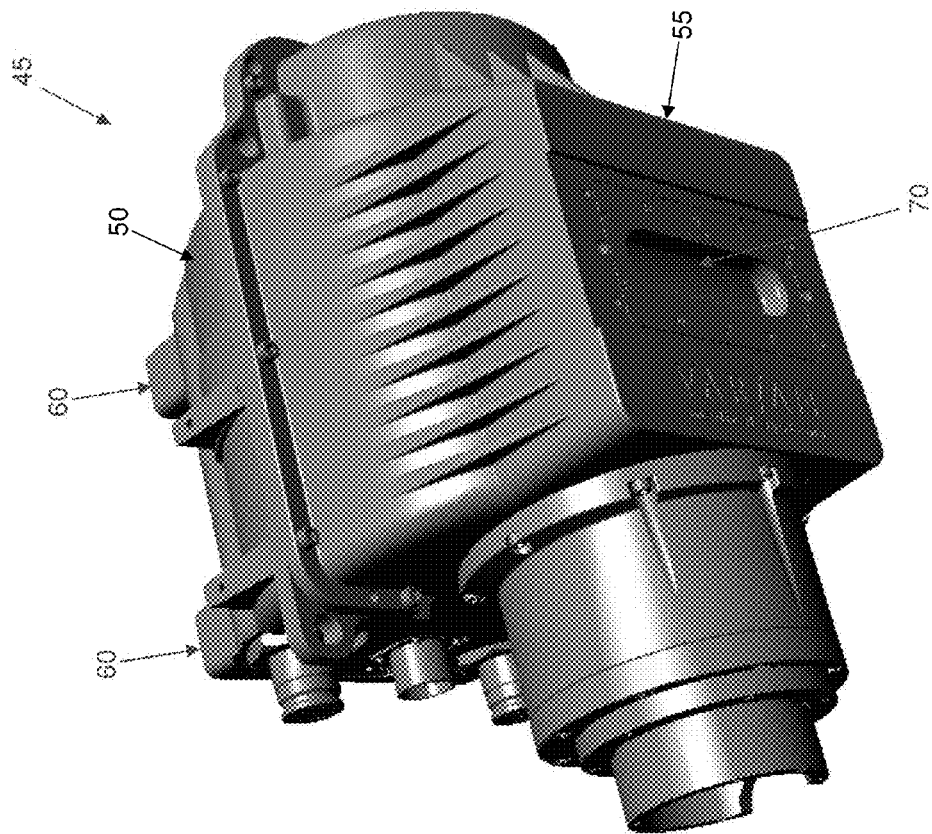
Figure 7:
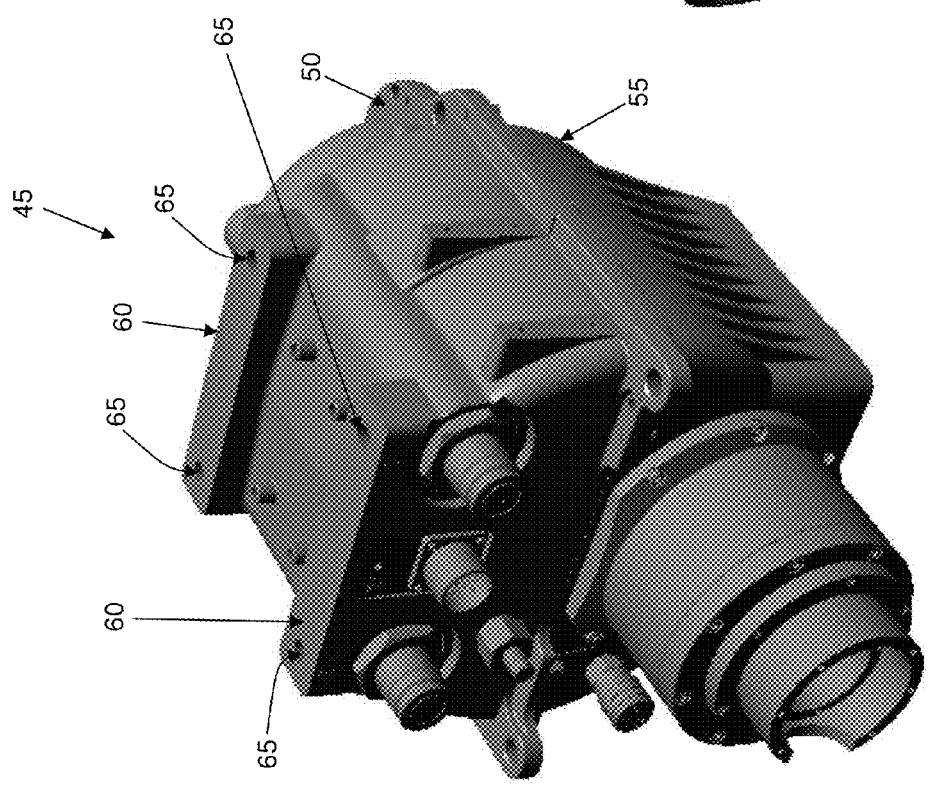
Figure 9:
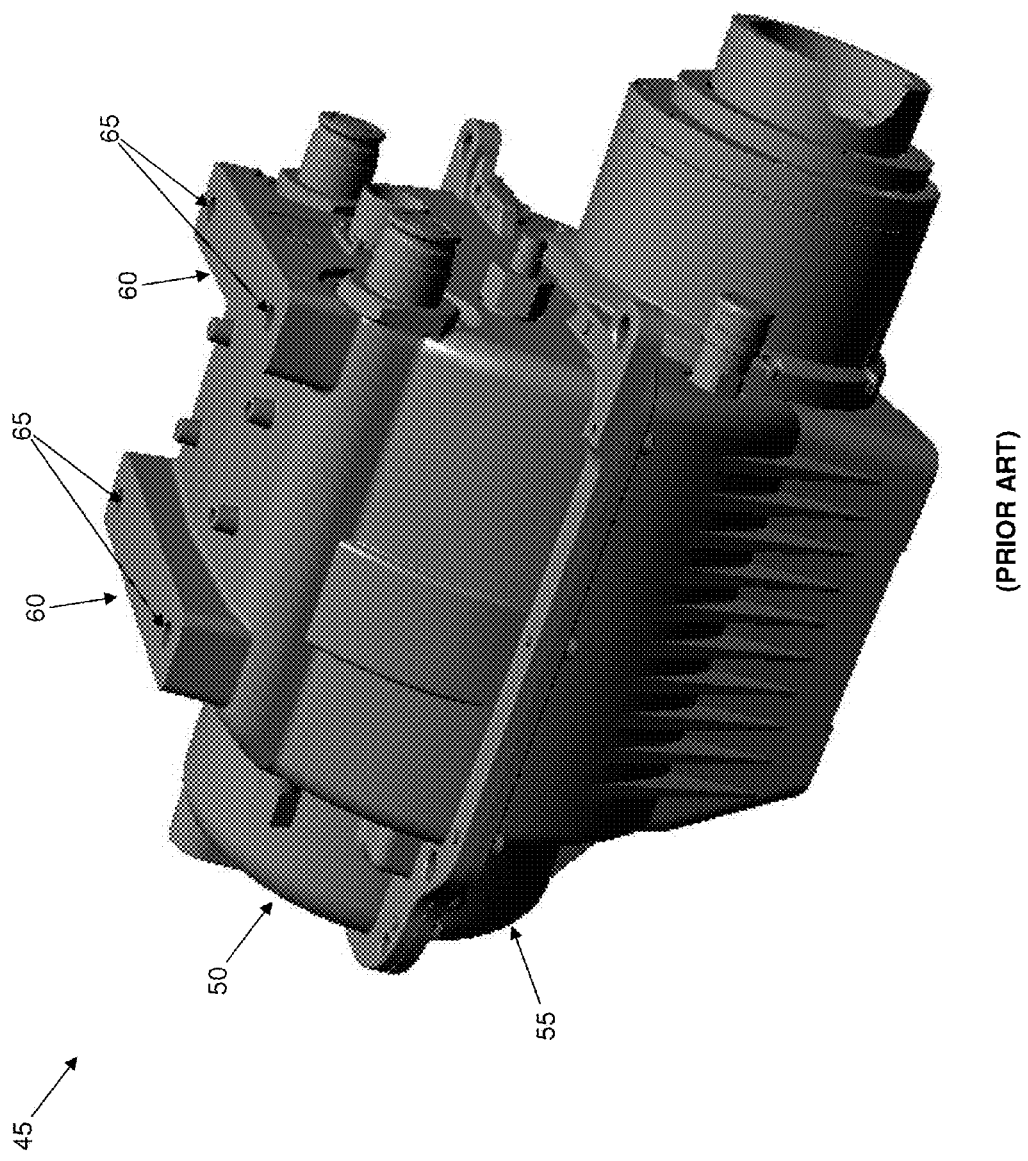
Figure 10:
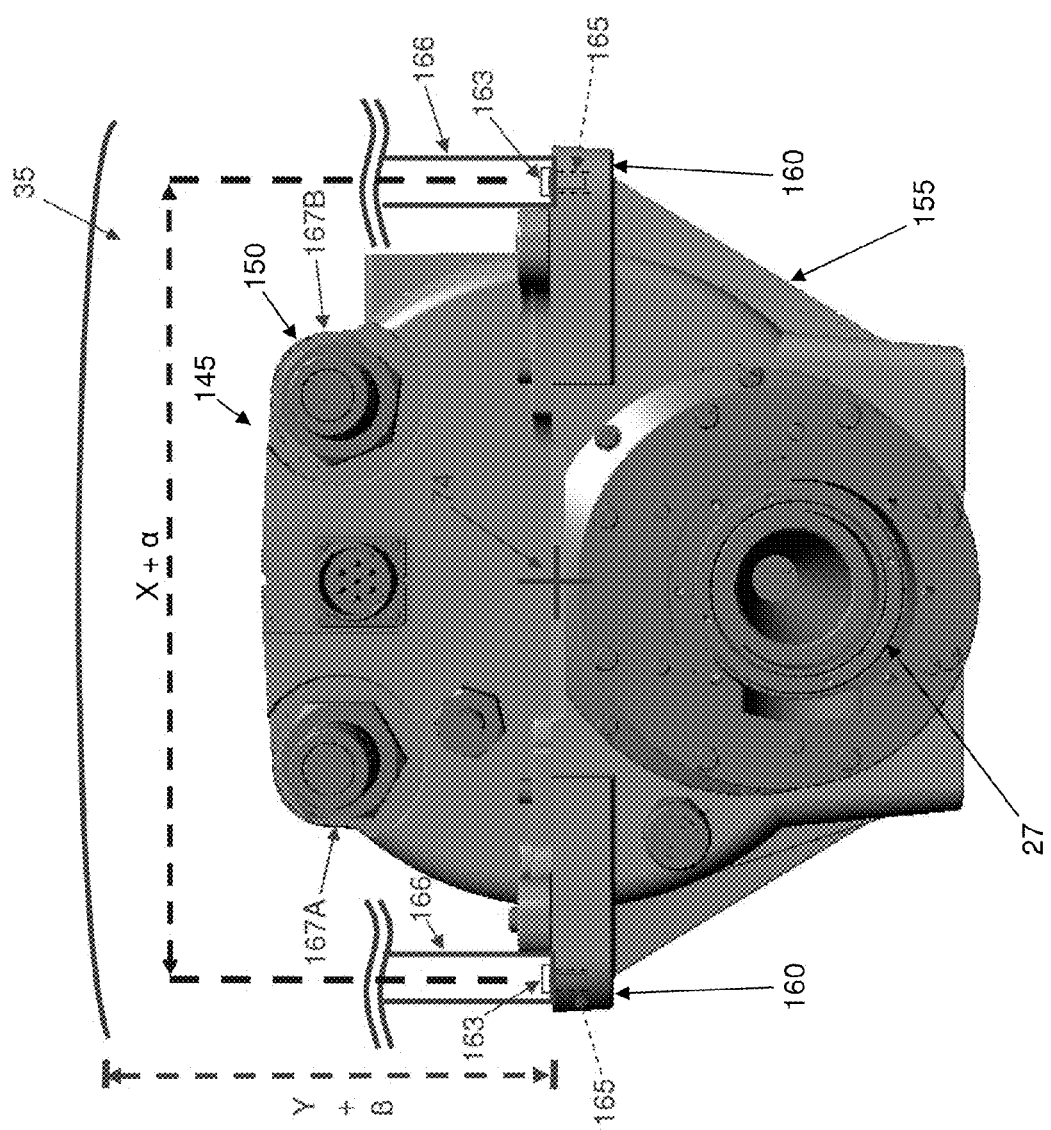
FIGS. 10-15 are schematic views showing a new and improved X-ray tube mount formed in accordance with the present invention for mounting an X-ray tube assembly to the rotating disk assembly of a CT imaging system.
Figure 11:
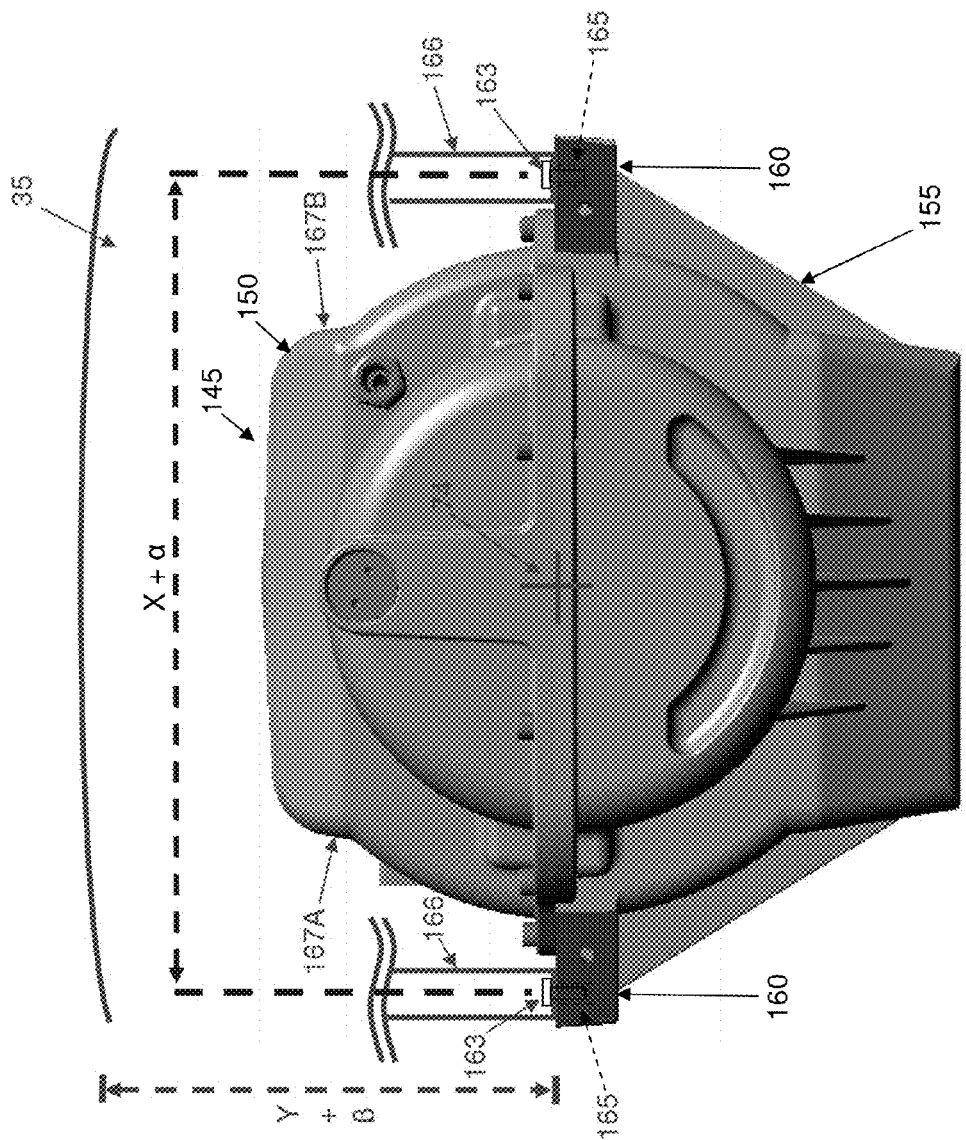
Figure 12:
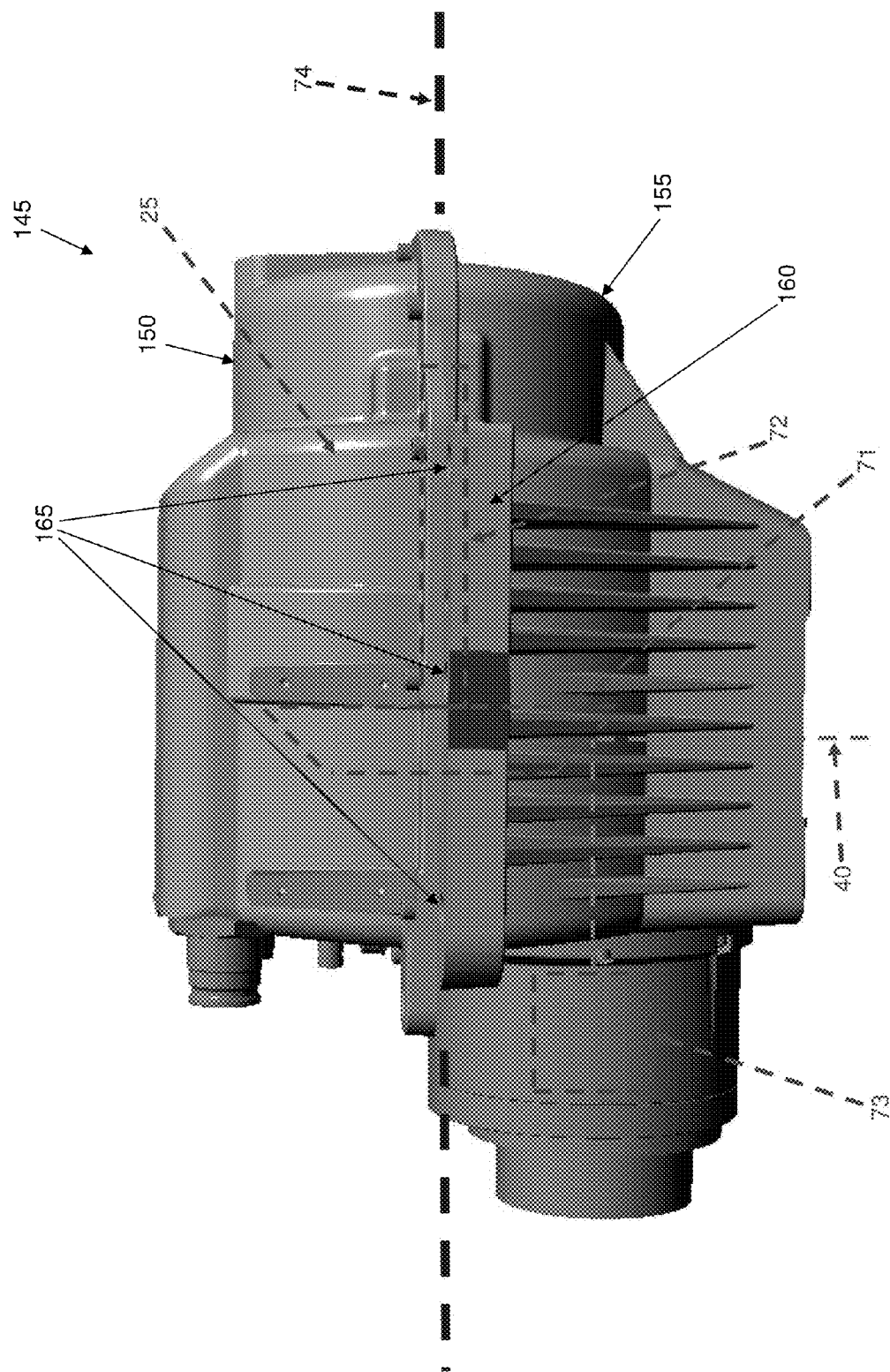
Figure 14:
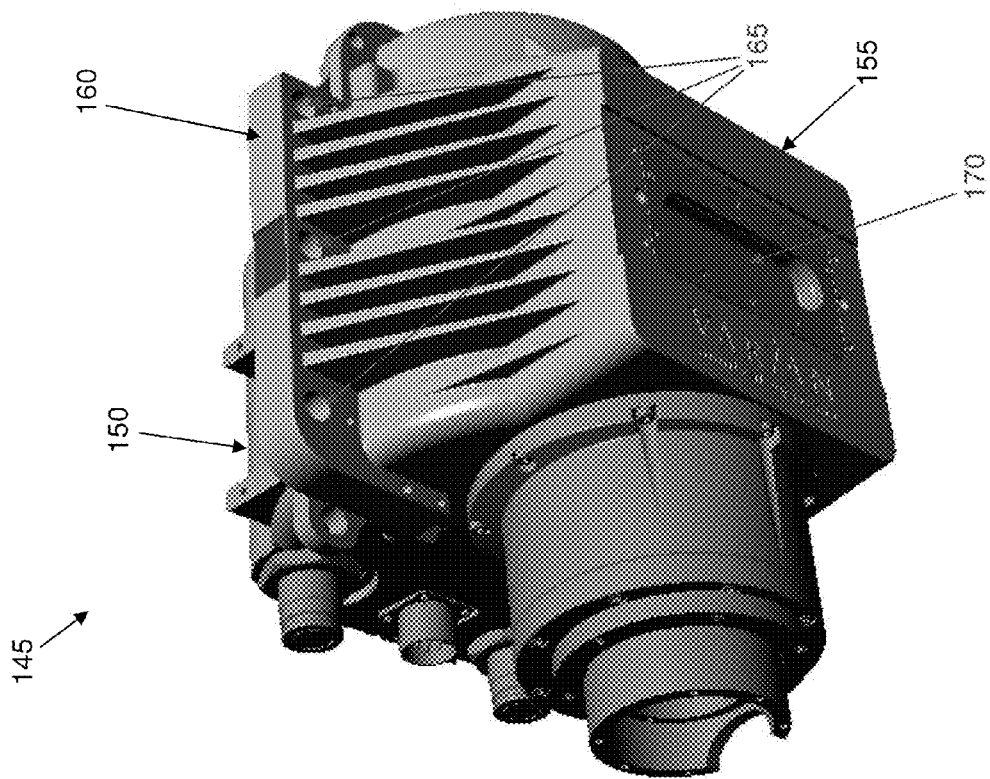
Figure 13:
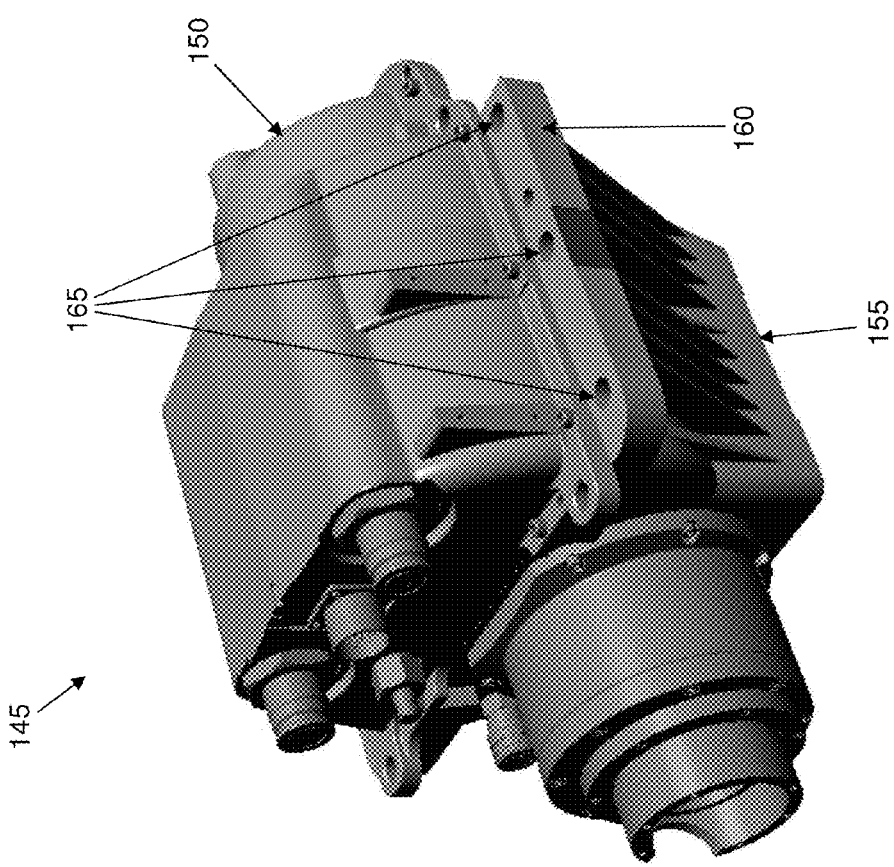
Figure 15:
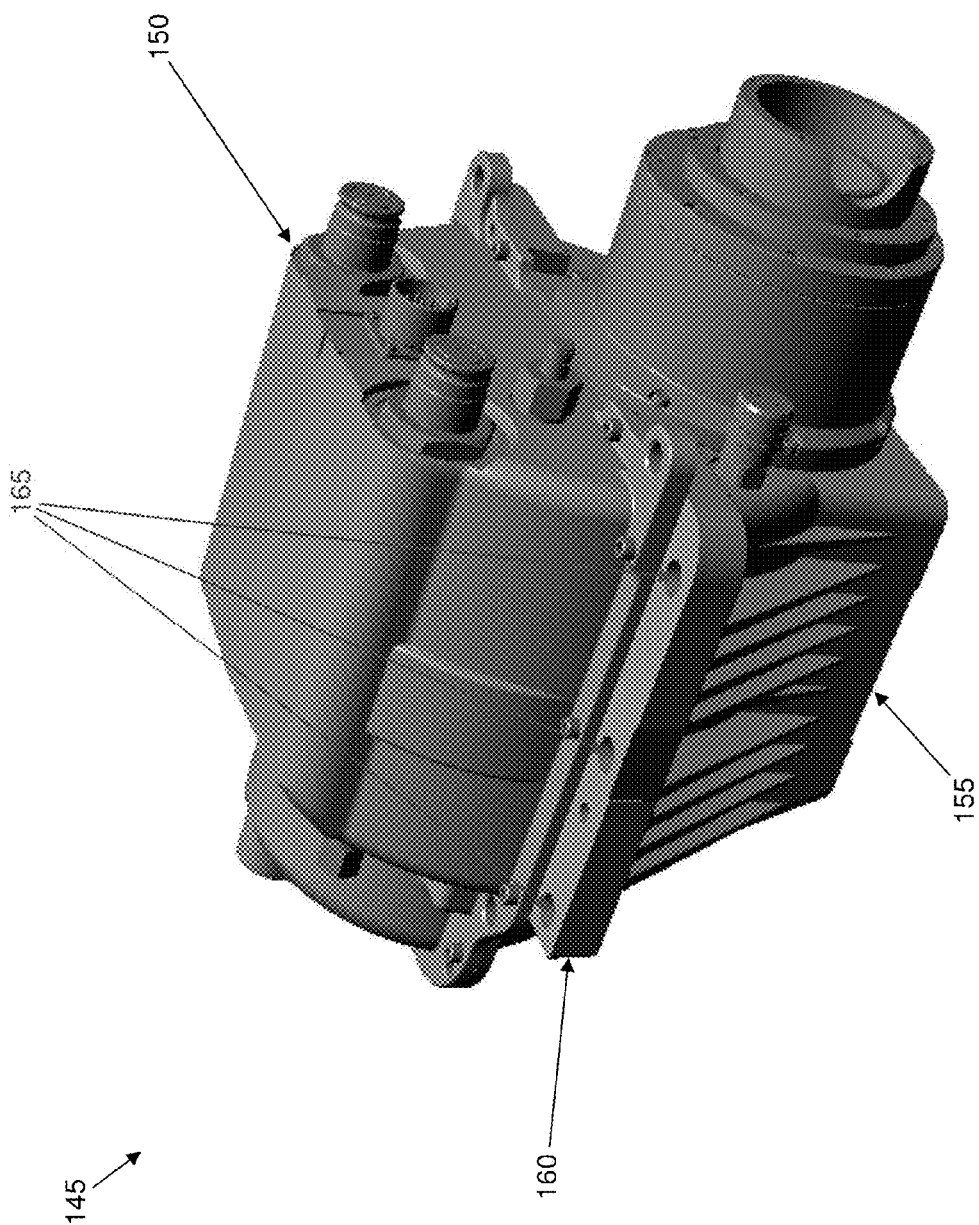

Significantly, holes 165 in flanges 160 of the new and improved X-ray tube mount 145 are disposed outboard of holes 65 in feet 60 of conventional X-ray tube mount 45 (note the distance X in FIGS. 4 and 5 versus the distance X+α in FIGS. 10 and 11), and holes 165 in flanges 160 of improved X-ray tube mount 145 are disposed closer to the center of rotation of rotating disk assembly 35 than holes 65 in feet 60 of conventional X-ray tube mount 45 (note the distance Y in FIGS. 4 and 5 versus the distance Y+β in FIGS. 10 and 11), whereby to provide significantly increased stability for X-ray tube assembly 25.

Furthermore, holes 165 in flanges 160 of improved X-ray tube mount 145 are set on a line which extends parallel to the longitudinal axis of X-ray tube assembly 25 (i.e., parallel to the axis of rotation 74 of anode 71 of X-ray tube assembly 25), which results in significantly increased stability for X-ray tube assembly 145 as rotating disk assembly 35 is rotated.

Thus it will be seen that with the present invention, (i) the mounting constructs of the new and improved X-ray tube mount 145 are moved laterally outward and radially inward relative to the mounting constructs of conventional X-ray tube mount 45 (see the distance X+α in FIGS. 10 and 11 versus the distance X in FIGS. 4 and 5, and see the distance Y+β in FIGS. 10 and 11 versus the distance Y in FIGS. 4 and 5), and (ii) the mounting constructs of the new and improved X-ray tube mount 145 are set on a line which extends parallel to the longitudinal axis of X-ray tube assembly 25 (i.e., parallel to the axis of rotation 74 of anode 71 of X-ray tube assembly 25), whereby to provide significantly more stability for X-ray tube assembly 25 as rotating disk assembly 35 of CT imaging system 5 is rotated.

Inner section 155 of X-ray tube mount 145 also includes a window 170 which emits the X-rays from X-ray tube assembly 25.

Figure 17:
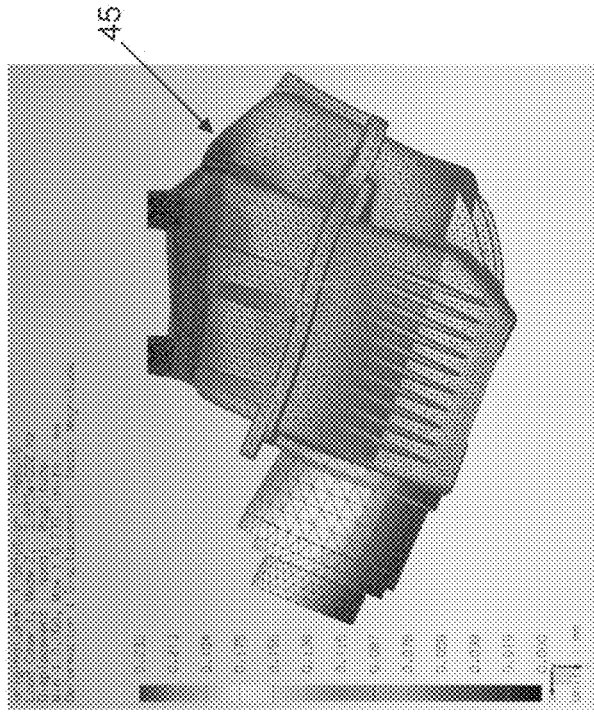
FIGS. 16 and 17 are schematic views showing the stiffness of the conventional X-ray tube mount shown in FIGS. 4-9.
Figure 16:
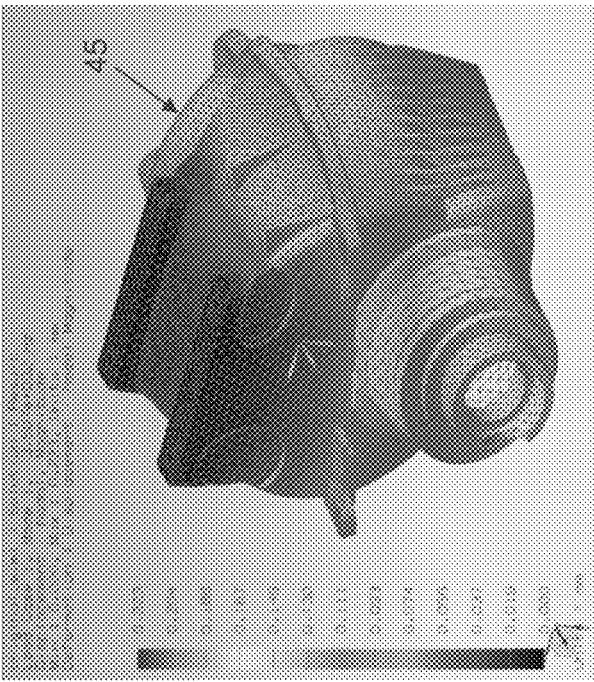
Figure 19:
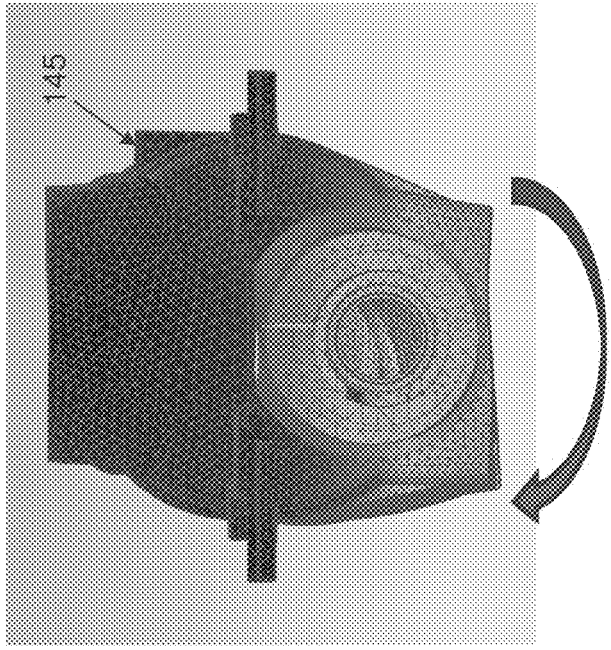
FIGS. 18 and 19 are schematic views showing the stiffness of the new and improved X-ray tube mount shown in FIGS. 10-15.
Figure 18:
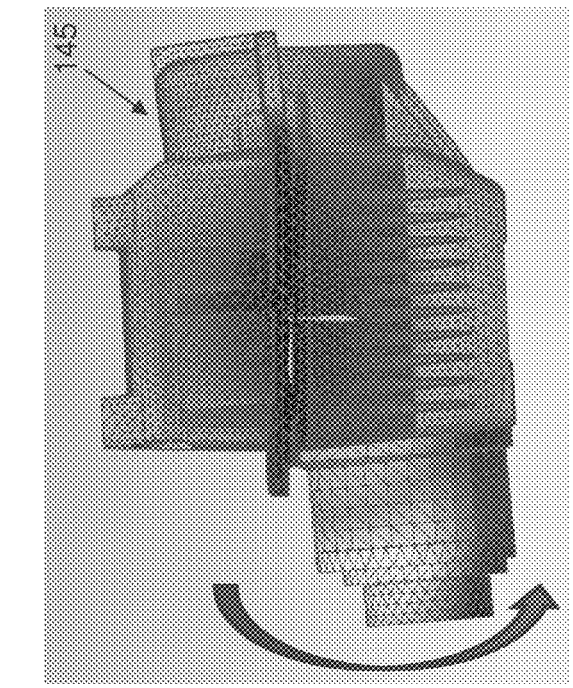

The new and improved X-ray tube mount 145 provides significantly more stability for X-ray tube assembly 25 than does conventional X-ray tube mount 45. See, for example, FIGS. 16 and 17, which show the extent of deformation of conventional X-ray tube mount 45, and FIGS. 18 and 19, which show the extent of deformation with the improved X-ray tube mount 145. As can be seen from FIGS. 16 and 17, and 18 and 19, the new and improved X-ray tube mount 145 provides significantly more stability for X-ray tube assembly 25 than does conventional X-ray tube mount 45.

It should also be appreciated that, if desired, flanges 160 may be formed on outer section 150 of X-ray tube mount 145, rather than being formed on inner section 155 of X-ray tube mount 145 as disclosed above. Of course, in this alternative construction, flanges 160 would be formed on the inner end of outer section 150 of X-ray tube mount 145, rather than being formed on the outer end of inner section 155 of X-ray tube mount 145 as previously disclosed.

It should also be appreciated that, if desired, improved X-ray tube mount 145 can also provide additional mounting means at the outermost surfaces of its outer section 150.

Modifications of the Preferred Embodiments

It should be understood that many additional changes in the details, materials, steps and arrangements of parts, which have been herein described and illustrated in order to explain the nature of the present invention, may be made by those skilled in the art while still remaining within the principles and scope of the invention.

What is claimed is:

1. An X-ray tube mount for mounting an X-ray tube assembly to a rotating disk assembly of a CT imaging system, wherein the X-ray tube assembly comprises an anode rotating on a shaft, the shaft having a longitudinal axis extending therethrough, said X-ray tube mount comprising:
    a housing for receiving the x-ray tube assembly, the housing having an inner end and an outer end, wherein said inner end of said housing is located closer to the center of rotation of the rotating disk assembly than said outer end of said housing; and
    at least two mounting constructs for mounting said housing to the rotating disk assembly, the at least two mounting constructs being connected to said housing at two points, wherein the two points are substantially co-planar with the longitudinal axis of the shaft.

2. An X-ray tube mount according to claim 1 wherein said at least two mounting constructs comprise a hole.

3. An X-ray tube mount according to claim 1 wherein the outer end of said housing terminates in first and second lateralmost edges, and further wherein said at least two mounting constructs are disposed more lateral than said first and second lateralmost edges of said outer end of said housing.

4. An X-ray tube mount according to claim 1 wherein said housing comprises an outer section terminating in said outer end and an inner section terminating in said inner end.

5. An X-ray tube mount according to claim 4 wherein said housing comprises at least one axially-extending flange, wherein said at least one axially-extending flange is formed on one of an inner portion of said outer section and an outer portion of said inner section, and further wherein one of said at least two mounting constructs is disposed on said at least one axially-extending flange.

6. An X-ray tube mount according to claim 5 wherein said at least one axially-extending flange is formed on said outer portion of said inner section.

7. An X-ray tube mount according to claim 5 wherein said housing comprises at least two axially-extending flanges, and further wherein at least one mounting construct is mounted to each axially-extending flange.

8. Apparatus comprising:
    an X-ray tube mount for mounting an X-ray tube assembly to a rotating disk assembly of a CT imaging system, wherein the X-ray tube assembly comprises an anode rotating on a shaft, the shaft having a longitudinal axis extending therethrough, said X-ray tube mount comprising:
a housing for receiving the x-ray tube assembly, the housing having an inner end and an outer end, wherein said inner end of said housing is located closer to the center of rotation of the rotating disk assembly than said outer end of said housing; and
at least two mounting constructs for mounting said housing to the rotating disk assembly, the at least two mounting constructs being connected to said housing at two points, wherein the two points are substantially co-planar with the longitudinal axis of the shaft; and
an X-ray tube assembly disposed within said housing.

9. A method for scanning an object, said method comprising:
providing a computer tomography (CT) imaging system comprising a rotating disk assembly having an axial opening formed therein, an X-ray tube assembly mounted to said rotating disk assembly on one side of said axial opening, and an X-ray detector assembly mounted to said rotating disk assembly on the opposing side of said axial opening, wherein said X-ray tube assembly comprises an anode rotating on a shaft, the shaft having a longitudinal axis extending therethrough, wherein said X-ray tube assembly is mounted to said rotating disk assembly using an X-ray tube mount, wherein said X-ray tube mount comprises:
a housing for receiving the x-ray tube assembly, the housing having an inner end and an outer end, wherein said inner end of said housing is located closer to the center of rotation of said rotating disk assembly than said outer end of said housing; and
at least two mounting constructs for mounting said housing to said rotating disk assembly, the at least two mounting constructs being connected to said housing at two points, wherein the two points are substantially co-planar with the longitudinal axis of the shaft;
positioning the object to be scanned within said axial opening of said rotating disk assembly; and
while rotating said rotating disk assembly, passing X-rays from said X-ray tube assembly through the object and detecting X-rays passing through the object with said X-ray detector assembly.

10. A method according to claim 9 wherein said at least two mounting constructs comprise a hole.

11. A method according to claim 9 wherein the outer end of said housing terminates in first and second lateralmost edges, and further wherein said at least two mounting constructs are disposed more lateral than said first and second lateralmost edges of said outer end of said housing.

12. A method according to claim 9 wherein said housing comprises an outer section terminating in said outer end and an inner section terminating in said inner end.

13. A method according to claim 12 wherein said housing comprises at least one axially-extending flange, wherein said at least one axially-extending flange is formed on one of an inner portion of said outer section and an outer portion of said inner section, and further wherein one of said at least two mounting constructs is disposed on said at least one axially-extending flange.

14. A method according to claim 13 wherein said at least one axially-extending flange is formed on said outer portion of said inner section.

15. A method according to claim 13 wherein said housing comprises at least two axially-extending flanges, and further wherein at least one mounting construct is mounted to each axially-extending flange.

\* \* \* \* \*